United States Patent
Singh et al.

(10) Patent No.: US 6,632,630 B2
(45) Date of Patent: Oct. 14, 2003

(54) MONOOXYGENASE ASSAYS

(75) Inventors: Sharat Singh, San Jose, CA (US); Ahmed Chenna, Sunnyvale, CA (US); Hossein Salimi-Moosari, Sunnyvale, CA (US); Ian Gibbons, Portola Valley, CA (US)

(73) Assignee: Aclara Biosciences, Inc., Mountain View, CA (US)

( * ) Notice: Subject to any disclaimer, the term of this patent is extended or adjusted under 35 U.S.C. 154(b) by 83 days.

(21) Appl. No.: 09/820,289

(22) Filed: Mar. 28, 2001

(65) Prior Publication Data

US 2002/0025545 A1 Feb. 28, 2002

Related U.S. Application Data

(60) Provisional application No. 60/193,034, filed on Mar. 29, 2000.

(51) Int. Cl.[7] .................................................. C12Q 1/26
(52) U.S. Cl. ......................... 435/25; 435/375; 435/968
(58) Field of Search ............................... 435/18, 19, 24, 435/25, 375, 968

(56) References Cited

U.S. PATENT DOCUMENTS

| 5,179,013 A | * | 1/1993 | Matsuoka et al. | ........... | 435/125 |
| 6,312,917 B1 | * | 11/2001 | Thakker et al. | ............... | 435/25 |

FOREIGN PATENT DOCUMENTS

| WO | WO 98/22502 | 5/1998 |
| WO | WO 99/65924 | 12/1999 |
| WO | WO 00/08169 | 2/2000 |
| WO | WO 00/12709 | 3/2000 |
| WO | WO 01/18046 | 3/2001 |

OTHER PUBLICATIONS

Crespi C. Microtiter Plate Assays for Inhibition of Human, Drug Metabolizing Cytochromes P450. Anal biochem 248(1)188–190, 1997.*
Nererkar P. Methoxyresorufin and Benzyloxyresorufin. Biochemical Pharmacology 46(5)933–943, 1993.*
Renauld A. Identification of in vitro Cytochrom P450 Modulators to Detect Induction by Prototype Inducers in the Mallard Duckling. Comparative Biochemistry and Physiology Part C 122(2)273–281, 1999.*
Mayer, R. T., et al., 7–Alkoxyquinolines: New Fluorescent Substrates for Cytochrome P450 Monooxygenases, *Biochemical Pharmacology*, vol. 40, No. 7, pp. 1645–1655, 1990.
Genbank Accession No. AL139324, Feb. 15, 2000.
Genbank Accession No. AI756825, Jun. 23, 1999.
Meden and Kuhn, "Overexpression of the oncogene c–crbB–2 (HER2/neu) in ovarian cancer: a new prognostic factor," *European Journal of Obstetrics & Gynecology and Reproductive Biology* 71:173–179, 1997.
Mayer, R. T., et al., "7–Alkoxyquinolines: New Fluorescent Substrates for Cytochrome P450 Monooxygenases, *Biochemical Pharmacology*, vol. 40, No. 7, pp. 1645–1655, 1990.
Crespi, C. L., et al., "Microtiter Plate Assays for Inhibition of Human, drug–metabolizing Cytochromes P450", *Analytical Biochemistry*, vol. 248, pp. 188–190, 1997.
Burke, M.D., et al., "Differential Effects of Phenobarbitone and 3 Methylcholanthrene Induction on the Hepatic Microsomal Metabolism and Cytochrome P–450 Binding of Phenoxazone and a Homologous Series of its n–Alkyl Ethers (Alkoxyresorufins)", *Chemico–Biological Interactions*, vol. 45, No. 2, pp. 243–258, 1983.
Anderson, J. M., "Fluorescent Hydrazides for the High–Performance Liquid Chromatographic Determination of Biological Carbonyls", *Analytical Biochemistry*, vol. 152, No. 1, pp. 146–153, 1986.
Guebitz, G., et al., "Fluorogenic Labelling of Carbonylcompounds with 7–Hydrazino–4–Nitrobenzo–2 Oxa–1, 3–Diazole", *Journal of Liquid Chromatography*, vol. 7, No. 4, pp. 839–854, 1984.
Copy of International Searh Report from Intl. Application No. PCT/US01/10155.

* cited by examiner

*Primary Examiner*—Ralph Gitomer
(74) *Attorney, Agent, or Firm*—Jacqueline F. Mahoney; Peter J. Dehlinger; Perkins Coie LLP

(57) ABSTRACT

Cytochrome P-450 assay methods and kits for the methods are provided employing a cytochrome P-450 enzyme, substrates characterized by having an oxidizable methylene group oxidized to an aldehyde and a fluorescent hydrazine. A fluorescent hydrazine is added to the reaction mixture and the resulting hydrazone analyzed by capillary electrophoresis. The method finds use in evaluating compounds for enzyme modulating activity.

13 Claims, 19 Drawing Sheets

MONOOXYGENASE ASSAYS

This application claims the benefit of U.S. Provisional Application No. 60/193,034 filed Mar. 29, 2000.

FIELD OF THE INVENTION

The field of this invention is monooxygenase assays.

BACKGROUND OF THE INVENTION

Monooxygenase include the numerous isoforms of the cytochrome P-450 enzymes. Because of the importance of these enzymes, particularly their activity in the liver, there is substantial interest in being able to assay for their activity and identify compounds that can modulate that activity. These enzymes serve to clear the blood of foreign factors. Unfortunately, in many cases these foreign factors are drugs, whose half-life is substantially diminished by virtue of being processed by the P-450 enzymes into inactive products. Also, reduced or modified activity of the P-450 enzymes may lead to poisoning or sensitivity to various agents, which in the normal person would be rapidly detoxified. The enzyme preparations are very expensive and each enzyme has multiple binding sites. Thus, multiple assays have to be performed to screen the enzyme(s).

With the advent of nanotechnology, there is an increased ability to perform numerous chemical and physical operations with very small volumes. This opportunity comes with the requirement that determinations have enhanced sensitivity to detect the fewer molecules that are present to provide the detectable signal. Part of the increased sensitivity may come from more sensitive detectors, but these are usually more expensive and are not readily available in most laboratories. The other opportunity is to provide assays that are more efficient in providing for detectable products, uses compounds that are readily accepted by the enzymes as substrates, and provide products with a strong signal, for fluorescent compounds, a high emission efficiency.

There is, therefore, substantial interest in providing P-450 assays that are rapid, accurate and can be performed in small volumes with low levels of enzyme and expensive reagents.

BRIEF DESCRIPTION OF THE PRIOR ART

U.S. Pat. No. 5,179,013 and references cited therein describe assaying for novel cytochrome P-450 enyzmes. Assays for P-450 enzymes are also described in Schwaneberg, et al., Anal Biochem 1999, 1:269:359–66; Tremblay, et al., Anal Biochem 1999, 276:215–26; Jansen, et al., J Chromatogr B Biomed Appl 1996, 684:133–45 and Eguchi et al., Xenobiotica 1996, 26:755–63. Other references that may be of interest include Hartmann and Frotscher, Arch Pharm 1999, 332:358–62; Ubeaud, et al., Eur J. Pharm Sci 1999, 8:255–60; Ertl, et al., Toxicol Appl Pharmcol 1999, 157:157–65; and Sanderson, et al., Toxicol Appl Pharmacol 1996, 137:316–25.

SUMMARY OF THE INVENTION

Methods and compositions are provided for determinations of monooxygenase enzymes, particularly P-450 enzymes, using a substrate having an ether group comprising an oxidizable α-hydrogen, resulting in an aldehyde product. The aldehyde is reacted in situ with a fluorescent hydrazine and the resulting reaction mixture separated by capillary electrophoresis. The hydrazone product indicates the reaction occurrence and the area under the peak may be used for quantitation. Kits can be provided for performing the assay.

DESCRIPTION OF THE SPECIFIC EMBODIMENTS

Figure 1:
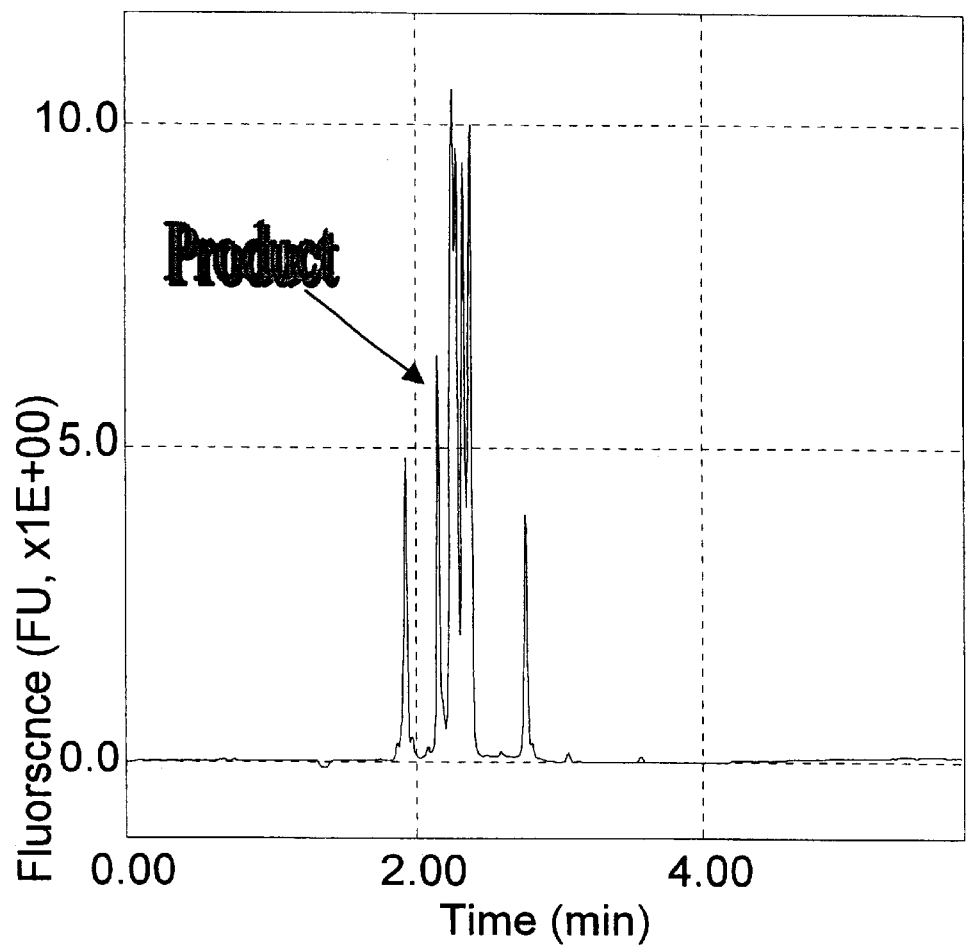
FIG. 1 shows an electropherogram of the reaction of benzaldehyde with fluorescein using capillary electrophoresis technique (PAGE)

Methods and compositions are provided for sensitive detection of monooxygenase activity, particularly the cytochrome P-450 enzyme isoforms, such as 3A4, 2E1, 1A2, 2A6, etc. The method employs an in vitro enzyme preparation, coenzyme, and at least one substrate. The substrates are characterized by having a turnover number under the conditions of the assay of $10^{-5}$, preferably at least about $10^{-3}$, min$^{-1}$, and comprising an ether, where one group is an aromatic compound, usually a heterocyclic compound, and the other group has an oxidizable α-hydrogen to produce an aldehyde (that is, the α-carbon atoms has two hydrogens). Where a mixture of substrates is included in the assay determination, each of the substrates will produce a product that will have a different mobility in the form of a fluorescent hydrazone. Prior to, during or after sufficient time for formation of the aldehyde product, a fluorescent hydrazine is added and the components of the reaction mixture separated under mildly acidic conditions by capillary electrophoresis.

A large number of monooxygenase substrates are known, which fulfill the desired requirements. The ethers are usually phenolic ethers, where the aromatic group may be carbocyclic or heterocyclic. Generally, the aromatic group will be at least about 4 carbon atoms, usually at least about 5 carbon atoms (6 annular members per ring) and not more than about 30 carbon atoms, usually not more than about 20 carbon atoms, and having from 0 to 8, usually 0 to 6 heteroatoms, which are for the most part O, N, S. Illustrative aromatic groups include phenyl, benzyl, naphthyl, acenaphthyl, coumarin, resorufin, quinoline, warfarin, methoxymephenytoin, mephenytoin, paclitaxel, debrisoquine, bufuralol, midazolam, in effect, any group which permits enzyme catalytic oxidation to result in a carbonyl. See, for example, Gentest Corp. 1999–2000 catalog (info @ gentest.com for further information.) The other group of the ether will have a methylene bonded to the oxygen of the ether, where the remaining moiety may be hydrogen, aliphatic, alicyclic, aromatic or heterocyclic. When other than hydrogen, the remaining moiety will be at least one carbon atom, usually at least about 2 carbon atoms and not more than about 16 carbon atoms, usually not more than about 12 carbon atoms. There may be from 0 to 4, usually 0 to 3 heteroatoms, such as O, S and N. The aldehyde reacts rapidly with a mono-substituted hydrazine with a change in the mobility of the hydrazine in capillary electrophoresis.

Specific substrates include 7-benzyloxyquinoline, 7-methoxyquinoline, AHMC, 7-benzyloxy-4-(trifluoromethyl)coumarin, 7-methoxy-4-(trifluoromethyl)coumarin, etc.

Various groups bonded to the methyleneoxy include methyl, substituted methyls, where the group bound to the ether oxygen is hydroxyethyl, ethyl ester of carboxymethyl, methoxypropyl, cyclohexylmethyl, benzyl and substituted benzyls, e.g. p-nitrobenzyl, p-cyanobenzyl, m-tolyl, o-anisole, etc.

The mono-substituted hydrazine will be substituted with a convenient fluorescer, where the hydrazone product will have a different mobility from the parent hydrazine. By employing a mildly acidic pH, the hydrazine will be protonated, while the hydrazone will be only partially, if at all, protonated. The difference in molecular weight and charge of the product in comparison to the hydrazine reactant provides for a significant change in mobility. Various fluorescers may be used, since the formation of the hydrazone is a secondary reaction and does not involve the P-450 enzyme. Selection of the fluorescer will be based on convenience, rate of reaction, water solubility, excitation and emission wavelengths and quantum yield (emission efficiency). Conventional fluorescers may be used, such as fluorescein, rhodamine, BODIPY, Texas Red, dansyl, Cascade blue, NBD, Cy-5, squarates, Lucifer yellow, Rhodol green, pyrene, acridine orange, etc.

In carrying out the assay, the enzyme concentration is conveniently in the range of about 1 nM to 500 nM, more usually in the range of about 25 to 250 nM and may vary outside the indicated range, depending upon the isoform of the cytochrome P-450. One may use an individual substrate or a mixture of substrates in order to determine the substrate profile of the enzyme. Each of the substrates would produce an aldehyde product that would have a different mobility when derivatized as a hydrazone. One could use homologous series, differential substitution, differences in charge and/or mass, or the like to obtain the different mobilities. A homologous series may include aliphatic molecules, aliphatic substituted aromatics or the like. Alternatively, one may have substituted benzenes, where one would have different substituents, such as halogen, oxy, amino, cyano, nitro, carboxy, e.g. esters, etc. Depending on the concentration of enzyme, nature of the substrate(s) and solubility in water, the turnover rate for each substrate, the rate of reaction of each of the products with the substituted hydrazine and its quantum yield, and the total number of substrates. The concentration range of each substrate will be about 50 to 5000 $\mu$M, more usually 100 to 2000 $\mu$M. Generally, the concentration of the substrate will be in the range of about 0.25 to 0.75 of $K_m$.

Coenzyme, if any, will be present in excess, so as not be rate limiting. Generally, with the concentrations of enzyme indicated above, the concentration of coenzyme will be at least about 0.1 mM, usually at least about 1 mM and not more than about 25 mM. The coenzyme solution should be prepared freshly for each series of determinations.

Various buffers may be used that do not interfere with the enzyme activity. These buffers include PBS, Tris, MOPS, HEPES, phosphate, etc. The pH will vary depending upon the particular monooxygenase being assayed, generally being in the range of about 7–7.5, where the pH is selected to provide for at least about maximum enzyme activity. The concentration of buffer will be sufficient to prevent a significant change in pH during the course of the reaction, generally being in the range of about 0.1 to 50 mM, more usually 0.5 to 20 mM.

The reaction time will usually be at least about 5 min, more usually at least about 30 min and not more than about 180 min, preferably not more than about 120 min, depending upon the temperature, concentrations of enzyme and substrate, etc. By using a specific time period for the reaction or taking aliquots at 2 different times, the rate of reaction can be determined for comparison with other determinations. The temperature will generally be in the range of about 20 to 50° C., more usually in the range of about 25 to 40° C.

In many instances, it may be advantageous to add a small amount of a non-ionic detergent. Generally the detergent will be present in from about 0.01 to 0.1 vol. %. Illustrative non-ionic detergents include the polyoxyalkylene diols, e.g. Pluronics, Tweens, Triton X-100, etc.

After sufficient time for a detectable amount of product, the reaction is quenched. Various quenching agents may be used, both physical and chemical. Conveniently, a small amount of a water-soluble inhibitor may be added, such as acetonitrile, DMSO, SDS, methanol, DMF, etc. The amount of inhibitor will vary with the nature of the inhibitor and may be determined empirically. A sufficient amount of the fluorescent hydrazine derivative is then added, usually at least stoichiometric, generally at least about 2-fold excess of the anticipated maximum amount of product, and may be 5-fold or more. Too much of the hydrazine should not be added, which can be determined empirically so as to avoid a broad band that might interfere in the separation from the hydrazone product. The hydrazone forming reaction is allowed to proceed for sufficient time for the reaction to be at least substantially complete and the reaction mixture is then separated using capillary electrophoresis under conventional conditions at a pH in the range of about 4–8, more usually 4–6, employing conventional buffers to achieve the pH, e.g. acetate, carbonate, EDPA, etc. The hydrazone peak is read and integrated to determine the activity of the enzyme. The conditions of the capillary electrophoresis are conventional and may be optimized for each hydrazone.

The fluorescent hydrazine derivatives are novel compounds. The compounds are N-($\alpha$-hydrazinylacyl)5-aminofluorescein, where the acyl group is of from 2 to 6, usually 2 to 4, carbon atoms. The product is made from 5-haloacetamidofluorescein and hydrazine.

The following examples are offered by way of illustration and not by way of limitation.

Experimental

TABLE 1

Results from the reaction of Fl-NH₂ and benzaldehyde

| Benzaldehyde Concentration (μM) | Incub. time (min) | Dilution | Peak Height | Peak Area | P H (Nor.) | P A (Nor.) | Migration time (min) |
|---|---|---|---|---|---|---|---|
| 133 | 30 | 50 | 6.297 | 10.212 | 6.297 | 10.212 | 2.153 |
| 133 | 200 | 50 | 4.791 | 11.818 | 4.072 | 10.045 | 2.533 |
| 33 | 30 | 50 | 0.886 | 2.134 | 0803 | 1.632 | 2.377 |
| 33 | 200 | 50 | 0.953 | 3.012 | 0.753 | 2.381 | 2.723 |
| 16 | 30 | 50 | 0.474 | 1.813 | 0.394 | 1.508 | 2.587 |
| 16 | 200 | 50 | 0.612 | 1.809 | 0.470 | 1.389 | 2.803 |
| 3 | 30 | 50 | 0.073 | 0.363 | 0.057 | 0.282 | 2.770 |
| 3 | 200 | 50 | 0.112 | 0.635 | 0.081 | 0.462 | 2.960 |
| Fl-NH₂ | — | 50 | 0.064 | 0.244 | 0.047 | 0.174 | 2.930 |
| 3 | 60 | 10 | 1.973 | 8.597 | 1.176 | 5.123 | 3.613 |
| 0.3 | 60 | 10 | 0.346 | 4.285 | 0.174 | 2.156 | 4.280 |
| Fl-NH₂ | — | 10 | 0.316 | 2.797 | 0.166 | 1.476 | 4.080 |

Reaction conditions were in phosphate buffer (3.3 mM and pH=5.6), fluorescein hydrazine ("Fl-NH$_2$") concentration was 1.6 mM, and 50 times dilution before injection: Separation buffer, phosphate (10 mM, pH=7.1): 27 cm capillary (I.D. 50 μm, O.D. 360 μm); pressure injection and 10 kV for separation. FIG. 1 shows an electropherogram of the reaction of benzaldehyde with fluorescein using capillary electrophoresis technique (PAGE).

Figure 2:
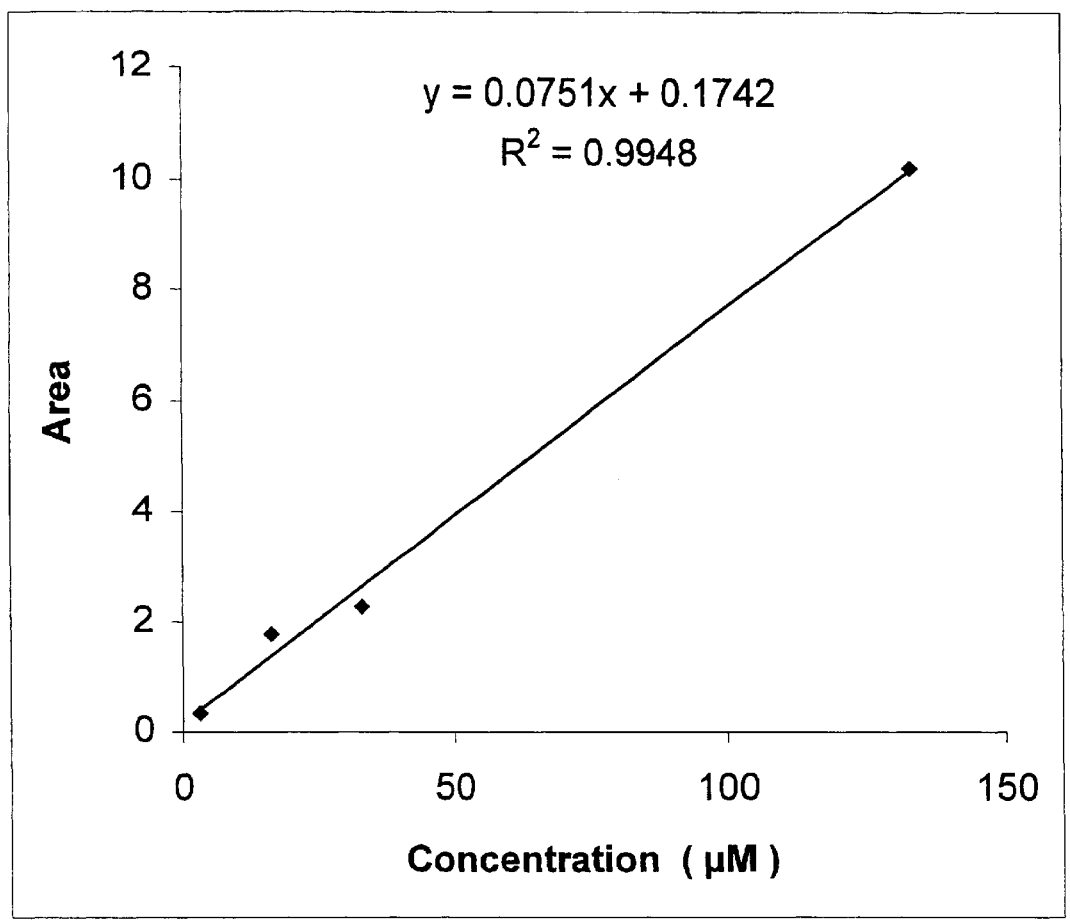
FIG. 2 shows a calibration curve for benzaldehyde and fluorescein hydrazine to form the hydrazone.
Figure 3:
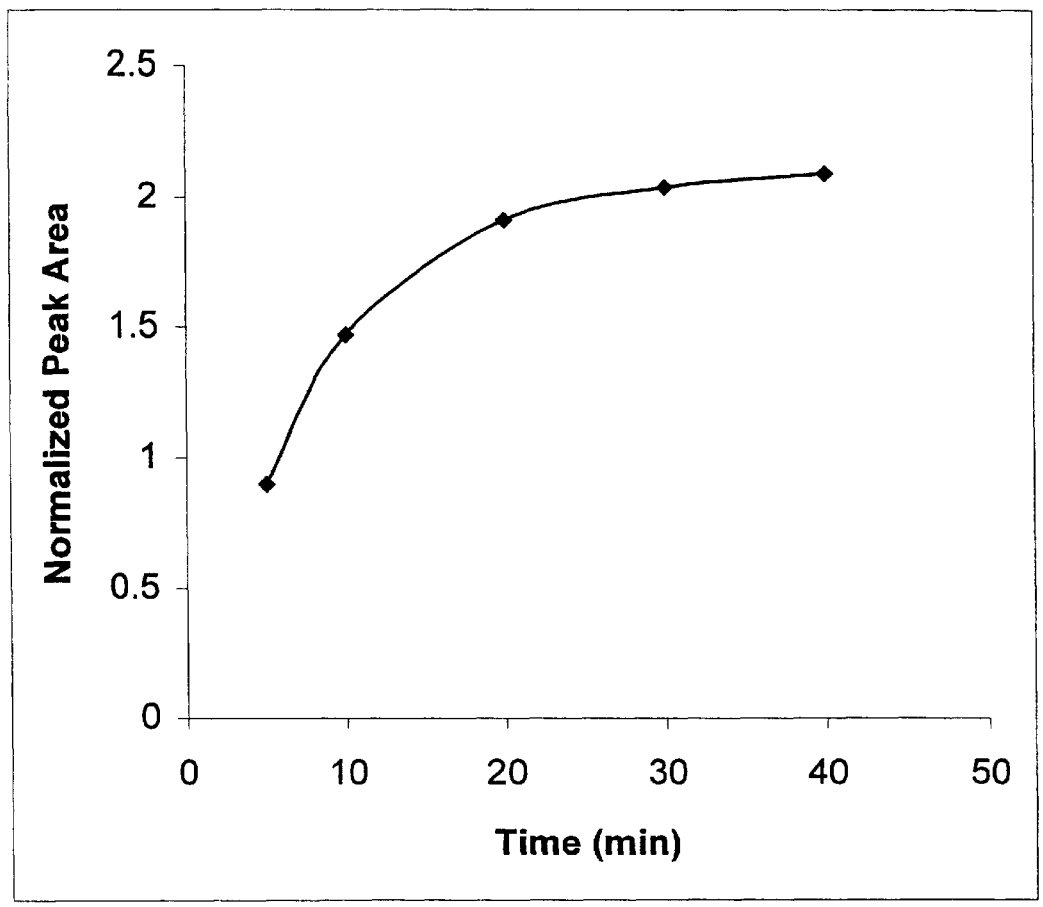
FIG. 3 is a graph of a kinetic study of the reaction between fluorescein-hydrazine and benzaldehyde.

A linear calibration curve was achieved for benzaldehyde (see FIG. 2) in the range of 3–133 μM (for 30 min incubation and 50 times dilution before the injection). Higher sensitivity was achieved with using lower dilution (see Table 1). The results from the kinetic study of this reaction are depicted in FIG. 3, which shows a maximum of reaction product is reached after 30 min and then levels off.

2-Cytochrome P-450 assay using CYP3A4: Micro titer plate. In order to evaluate the assay, two sets of substrates were chosen: the first one was 7-benzyloxyresorufin (7-BR) and the second one was 7-benzyloxyquinoline (7-BQ).

I: 7-Benzyloxyresoufin (7-BR)

Figure 4:
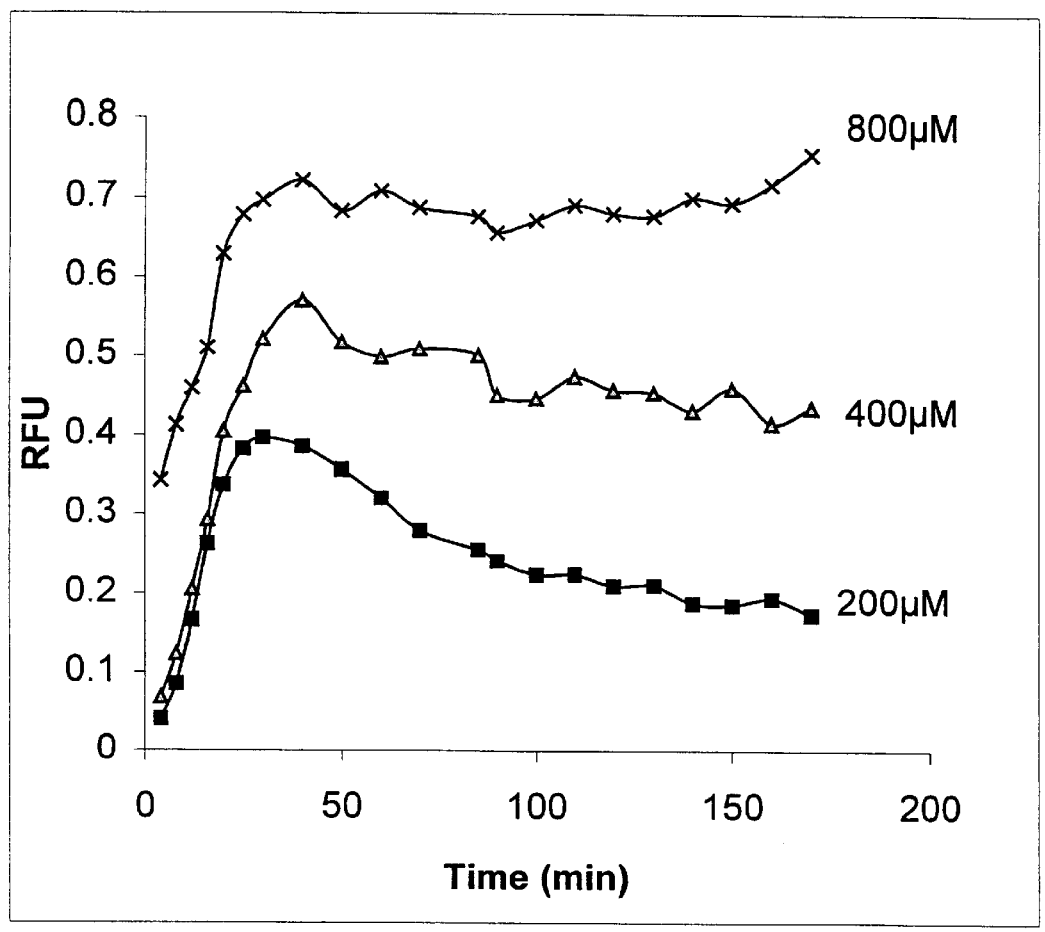
FIG. 4 is a graph of the effect of concentration of 7-benzyloxyresorufin on enzymatic activity.
Figure 5:
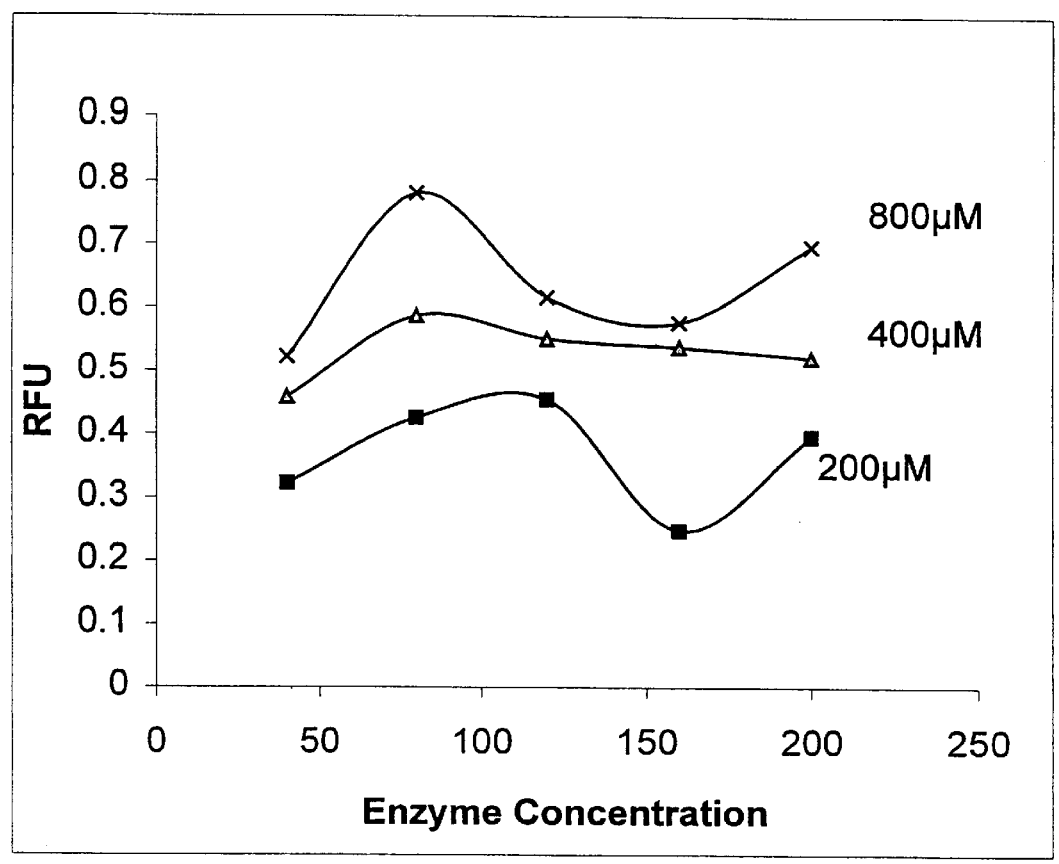
FIG. 5 is the effect of the enzyme concentration on enzymatic activity.
Figure 6:
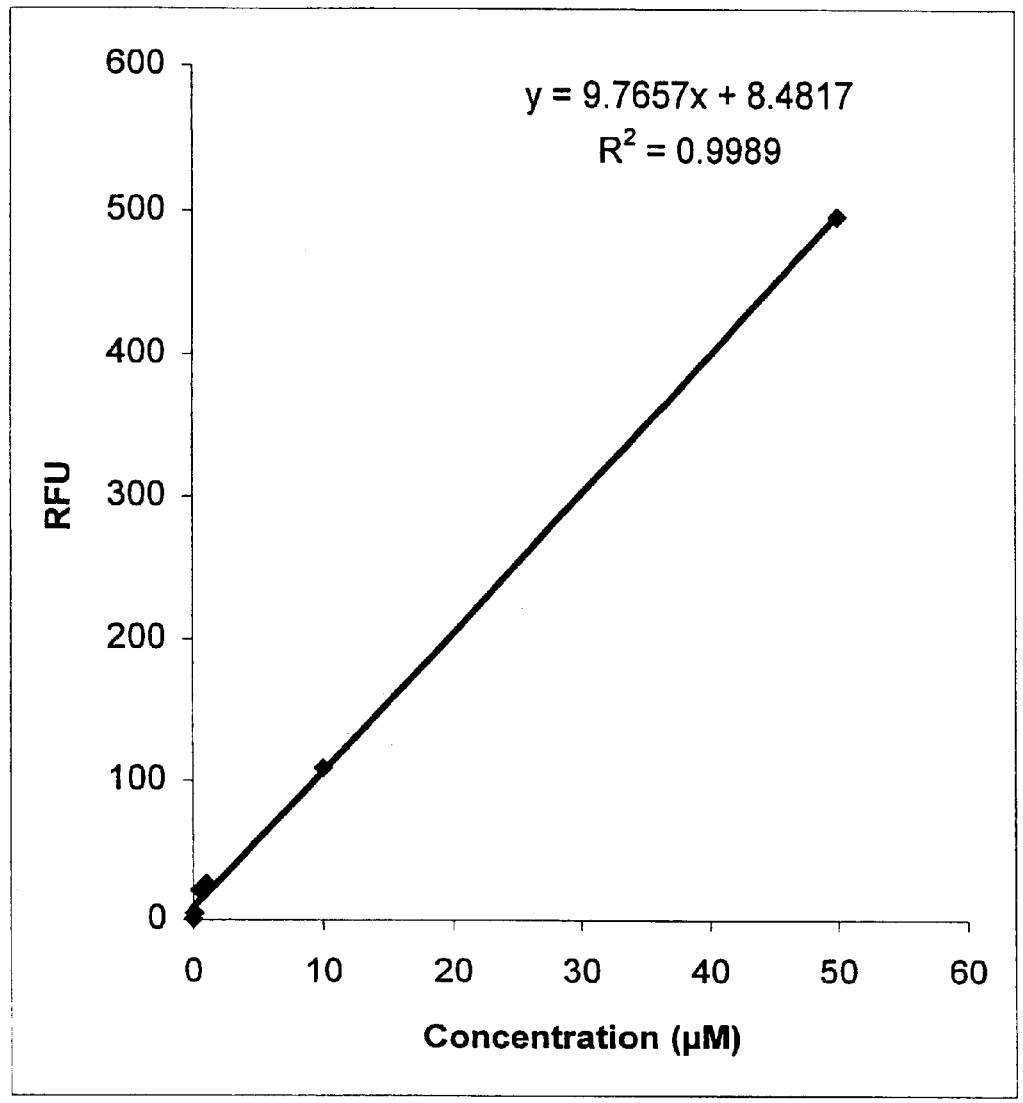
FIGS. 6A and 6B are two calibration curves over different concentration ranges for 7-benzyloxyresorufin.
Figure 6:
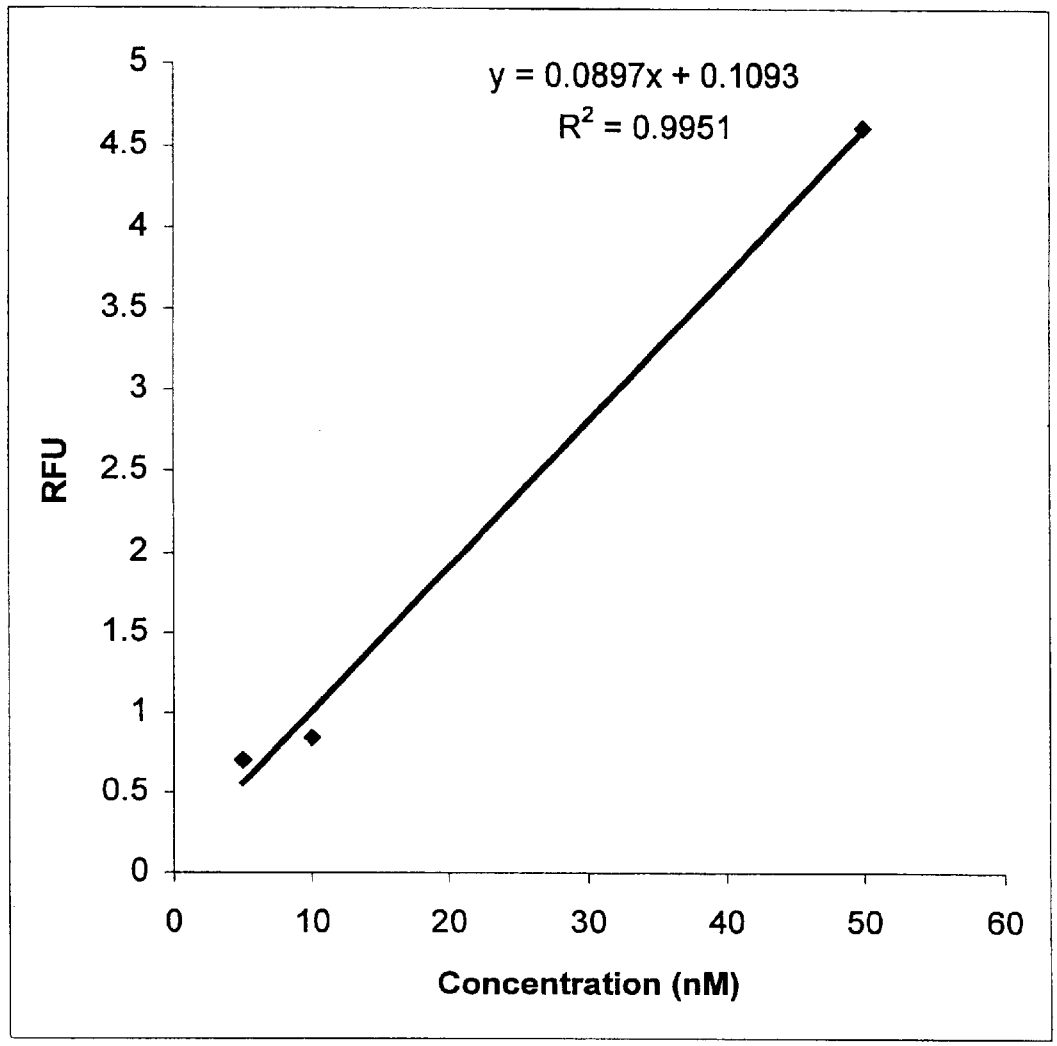

The effect of enzyme and substrate concentration as well as incubation time on the enzymatic activity for CYP3A4 was evaluated using a micro titer plate (reaction volume was 50 μl). The results from these studies are shown in FIGS. 4–6. FIG. 4 shows the effect of 7-BR concentration as a function of time (enzyme concentration was 200 nM). As can be seen, regardless of substrate concentration, reaction was reached to a maximum after 30–40 min and then leveled off. In addition, the activity increases significantly upon an increase in substrate concentration. FIG. 5 shows the effect of enzyme concentration on enzymatic activity for four different substrate concentrations. As can be seen in this Figure, the effect of enzyme concentration for this specific substrate is not that significant, since the reactivity of enzyme is limited by the solubility of the substrate (7-BR has a very limited solubility in water). FIGS. 6(A) and 6(B) show the calibration curve for resorufin (product of enzymatic activity) over a concentration range of 5–50,000 nM.

II: 7-Benzyloxyquinoline (7-BQ)

The effect of enzyme and substrate concentration as well as incubation time on the enzymatic activity for CYP3A4 and 7-BQ was evaluated using a micro titer plate (reaction volume was 50 μl). The results from these studies are shown in FIGS. 7–8.

Figure 7:
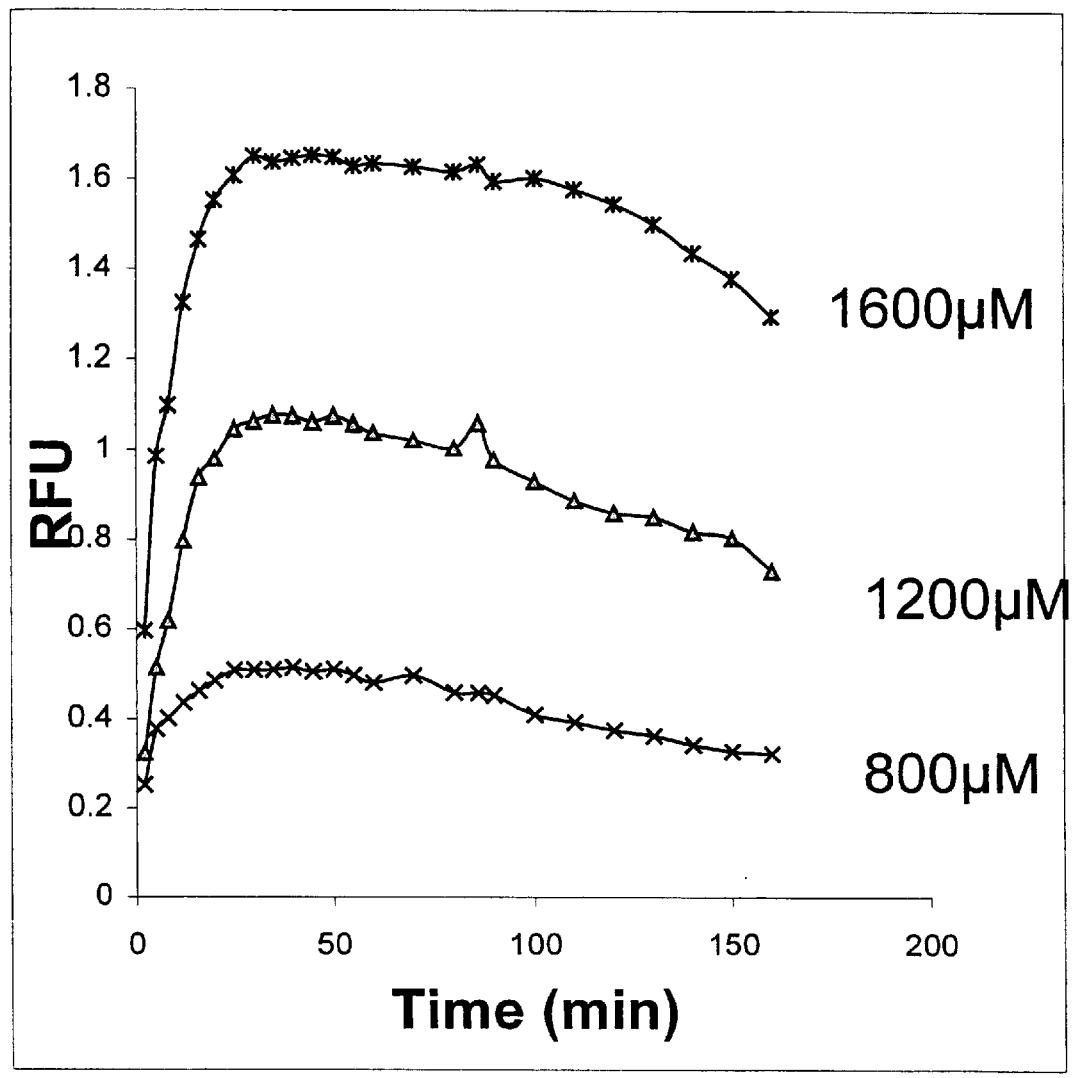
FIGS. 7 and 8 are graphs of the effect of concentration of 7-benzyloxyquinoline and enzyme, respectively, on enzymatic activity.
Figure 8:
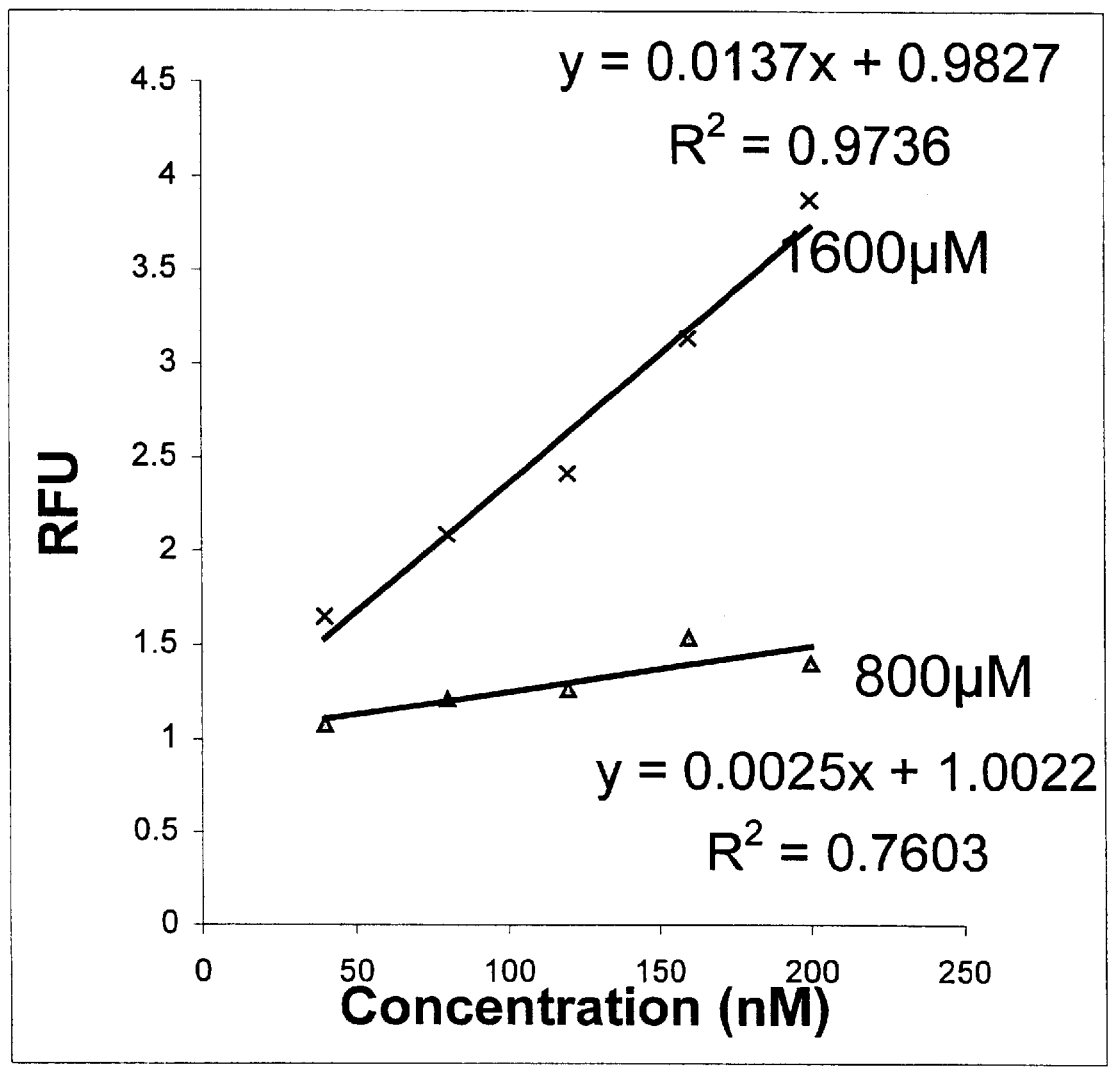

FIG. 7 shows the effect of 7-BQ concentration as a function of time (enzyme concentration was 40 nM). As can be seen, regardless of substrate concentration, the reaction reached a maximum after 25–30 min and then leveled off. In addition, the activity, as in the case of 7-BR, increases significantly upon an increase in substrate concentration. FIG. 8 shows the effect of enzyme concentration on enzymatic activity for four different substrate concentrations. As can be seen in this Figure, an increase of enzyme concentration will cause an increase in the enzymatic activity for this specific substrate.

III. Effect of Pluronic F68

Figure 9:
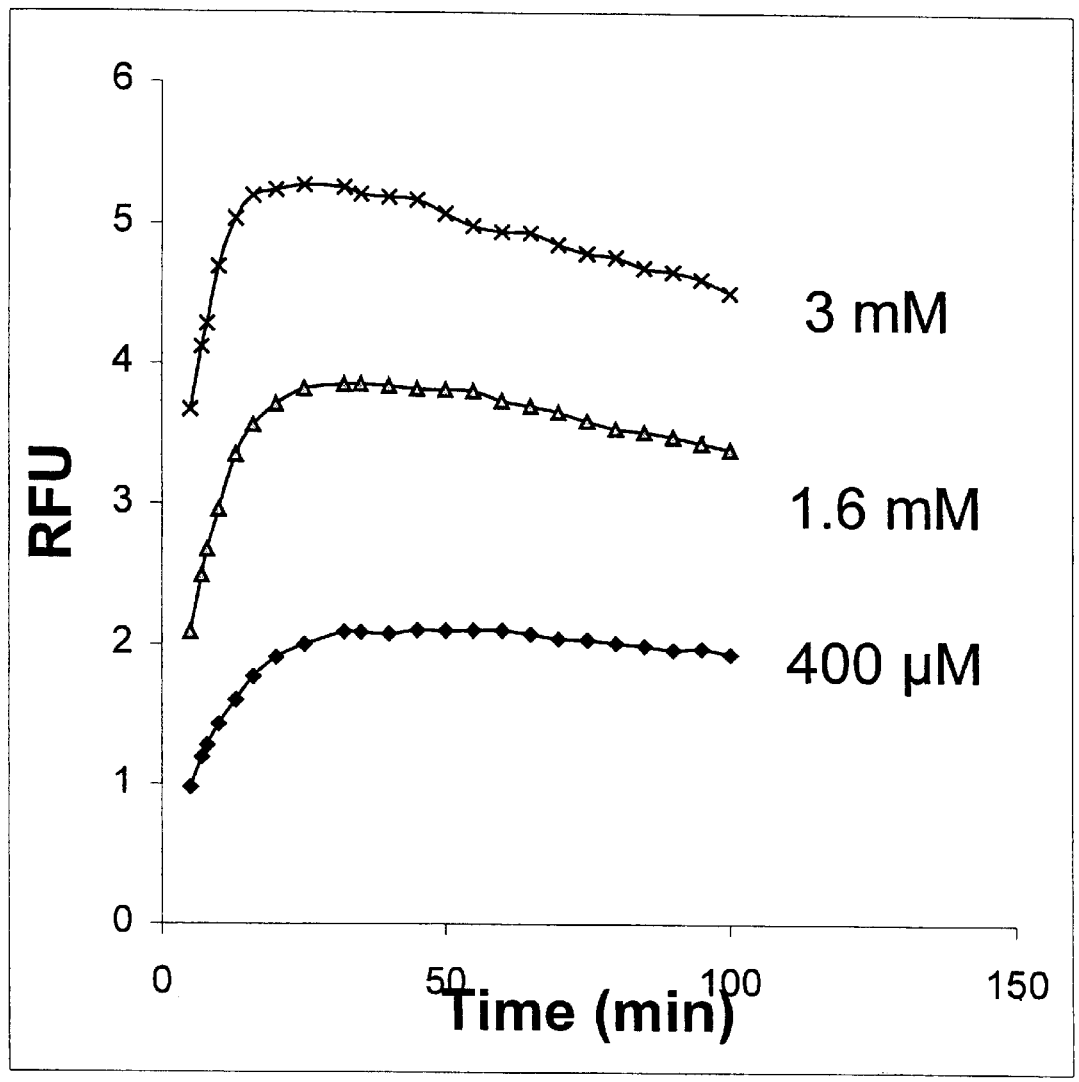
FIGS. 9 and 10 are graphs of the effect of a non-ionic detergent on enzymatic activity with 7-benzyloxyquinoline as the substrate, with varying concentration of substrate enzyme.
Figure 10:
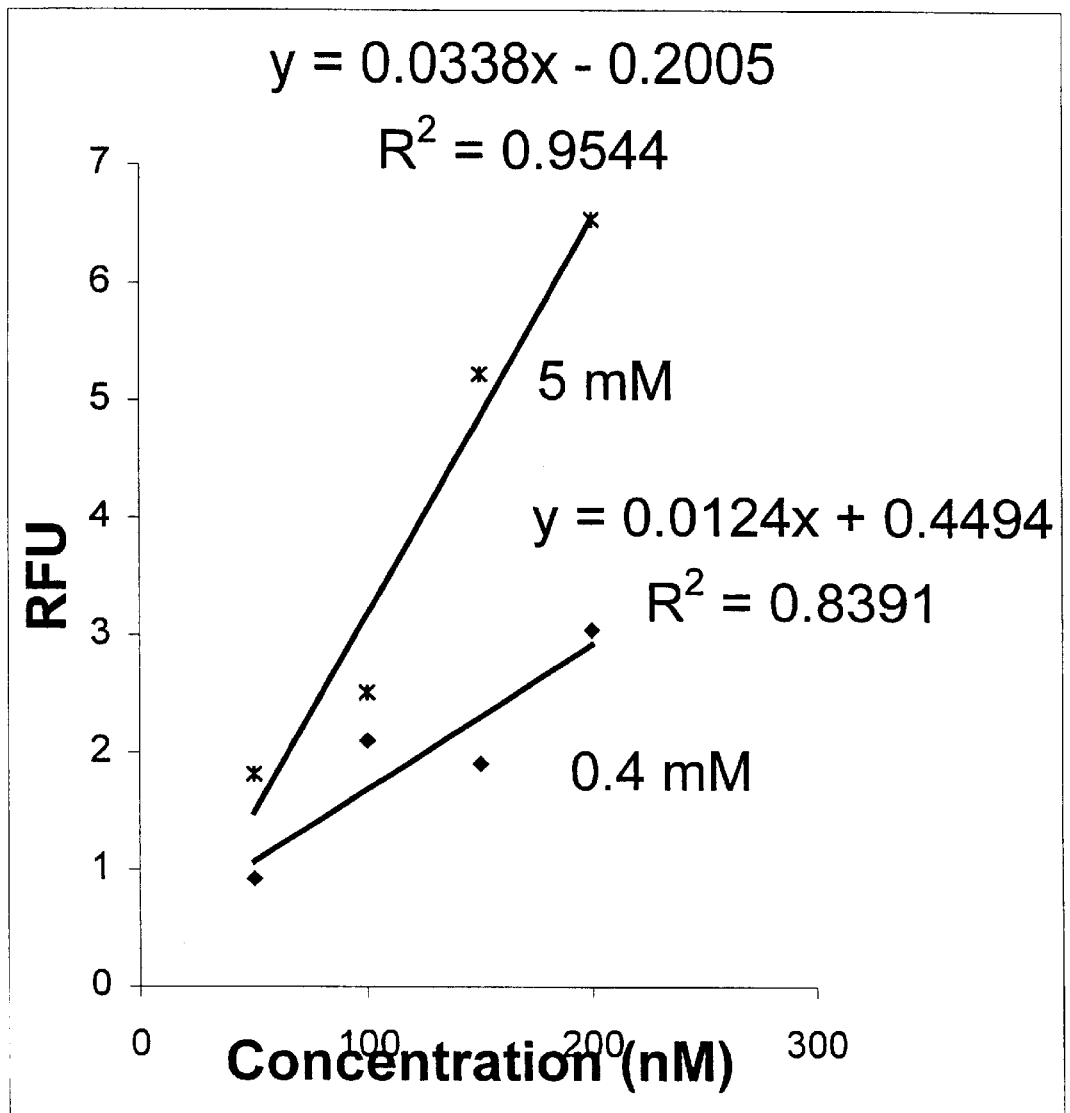
Figure 11:
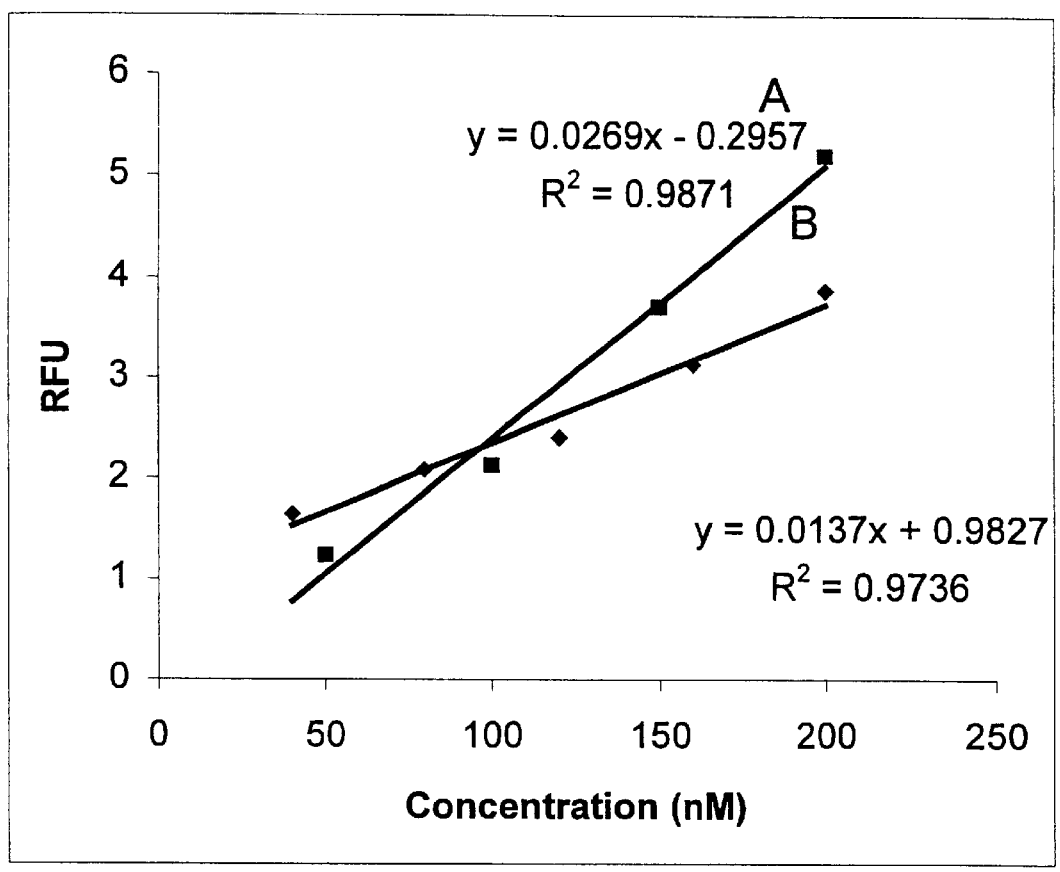
FIG. 11 is a graph of comparison calibration curves in the presence of a nonionic detergent.

The effect of the addition of Pluronic F68 on the enzymatic activity of CYP3A4 using 7-BQ as a substrate on a micro titer plate was studied. The results from these studies are shown in FIGS. 9–11. FIG. 9 shows the effect of 7-BQ concentration as a function of time (enzyme concentration was 150 nM). As can be seen, regardless of substrate concentration, reaction reached to a maximum after 25 min and then leveled off. In addition, the activity, like in the previous cases, increases significantly upon an increase in substrate concentration. FIG. 10 shows the effect of enzyme concentration on enzymatic activity for three different substrate concentrations. As can be seen in this Figure, an increase in enzyme concentration will cause an increase in the enzymatic activity. FIG. 11 shows a comparison between the effect of the presence (A) and absence (B) of Pluronic F68 on the enzymatic activity of CYP3A4. Comparing the slopes of these two calibration curves shows a 96% increase in the enzymatic activity upon an addition of 0.026% of Pluronic F68.

Figure 12:
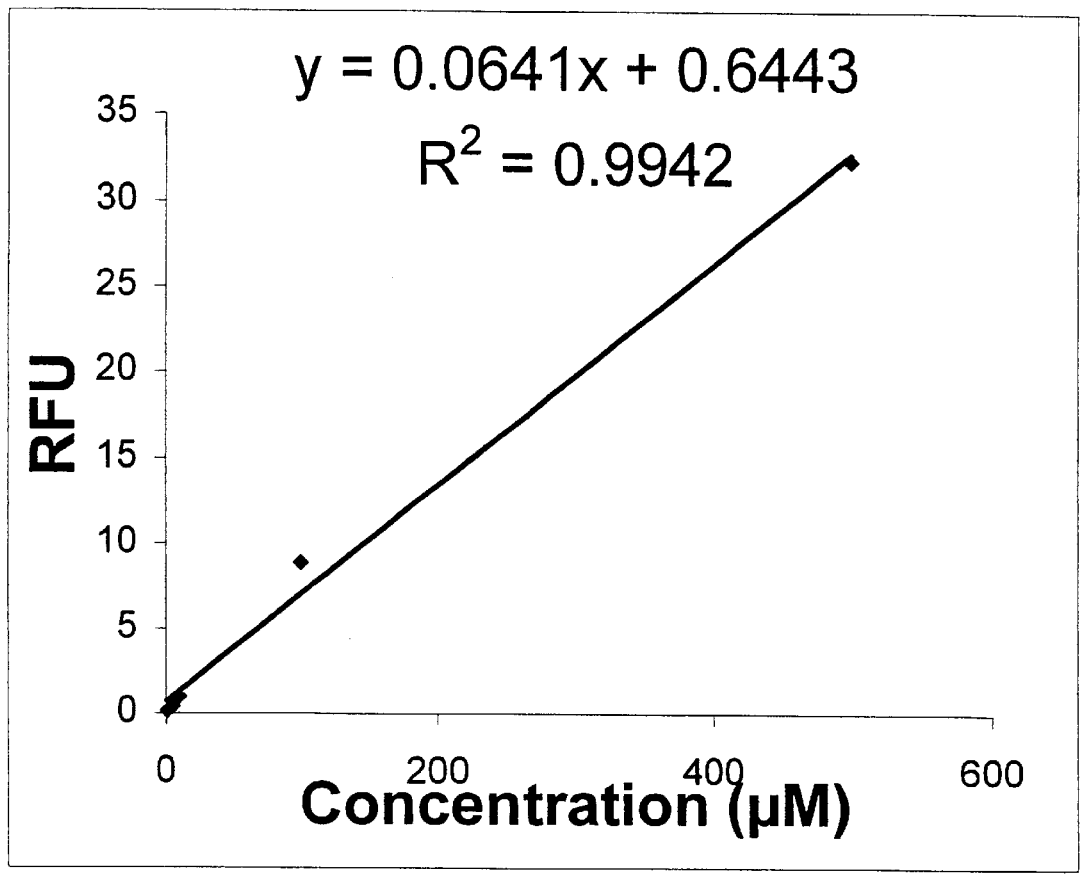
FIG. 12 is a calibration curve for 7-hydroxyquinoline.

FIG. 12 shows the calibration curve for 7-Hydroxyquinoline (product of enzymatic activity) over a concentration range of 1–500 μM.

The following table shows a comparison of the turnover rates (TO) between resorufin and 7-BQ, which shows a significantly higher number for 7-BQ as compared to resorufin. $2.45 \times 10^{-3} \pm 1.9 \times 10^{-3}$ min$^{-1}$; 7-BQ 17±11 min$^{-1}$.

CYP450 Assay Using Fl-NH$_2$ as a Universal Substrate and Capillary Electrophoresis I-Assay protocol.

1. Enzymatic reaction. The reaction mixture contains 10 μl of buffer solution for CYP3A4 (provided by PanVera, pH=7.4), 10 μl of enzyme CYP3A4 (PanVera), 1 μl 7-BQ (20 mM), 29 μl of water, and 10 μl of a fresh solution of NADPH (10 mM). The reaction mixture was incubated for 120 min at 37° C. after the addition of NADPH. Then the reaction was stopped by an addition of 10 µl of acetonitrile followed by a 2 µl addition of Fl-NH$_2$ (5 mM). Separation conditions were: buffer, 10 mM Acetate and 5 mM SDS (pH= 4.95); 27 cm capillary (I.D. 50 µm, O.D. 360 µm); Pressure injection for 5 s and 20 kV for separation.

2. Control 1 (no enzyme). The reaction mixture was prepared containing 10 µl of Buffer (pH=7.4, provided from PanVera for CYP3A4), 29 µl of water, 1 µl of 7-BQ (20 mM), and 10 µl NADPH (10 mM), then incubated for 2 h at 37 ° C., followed by an addition of 10 µl of acetonitrile to stop the reaction followed by a 2 µl addition of Fl-NH$_2$ (5 mM).

3. Control 2 (no NADPH). The reaction mixture was prepared containing 10 µl of Buffer (pH=7.4, provided from PanVera for CYP3A4), 10 µl of CYP3A4 (PanVera), 29 µl of water, and 1 µl of 7-BQ (20 mM), then incubated for 2 h at 37° C. followed by an addition of 10 µl of acetonitrile to stop the reaction followed by a 2 µl addition of Fl-NH$_2$ (5 mM).

4. Control 3 (no 7-BQ). The reaction mixture was prepared containing 10 µl of buffer solution for CYP3A4 (provided by PanVera, pH=7.4), 10 µl of enzyme CYP3A4 (from PanVera), 20 µl of water, and 10 µl of a fresh solution of NADPH (10 mM), and was incubated for 120 min at 37° C. after the addition of NADPH. Then the reaction was stopped by an addition of 10 µl of acetonitrile followed by a 2 µl addition of Fl-NH$_2$ (5 mM).

Figure 13:
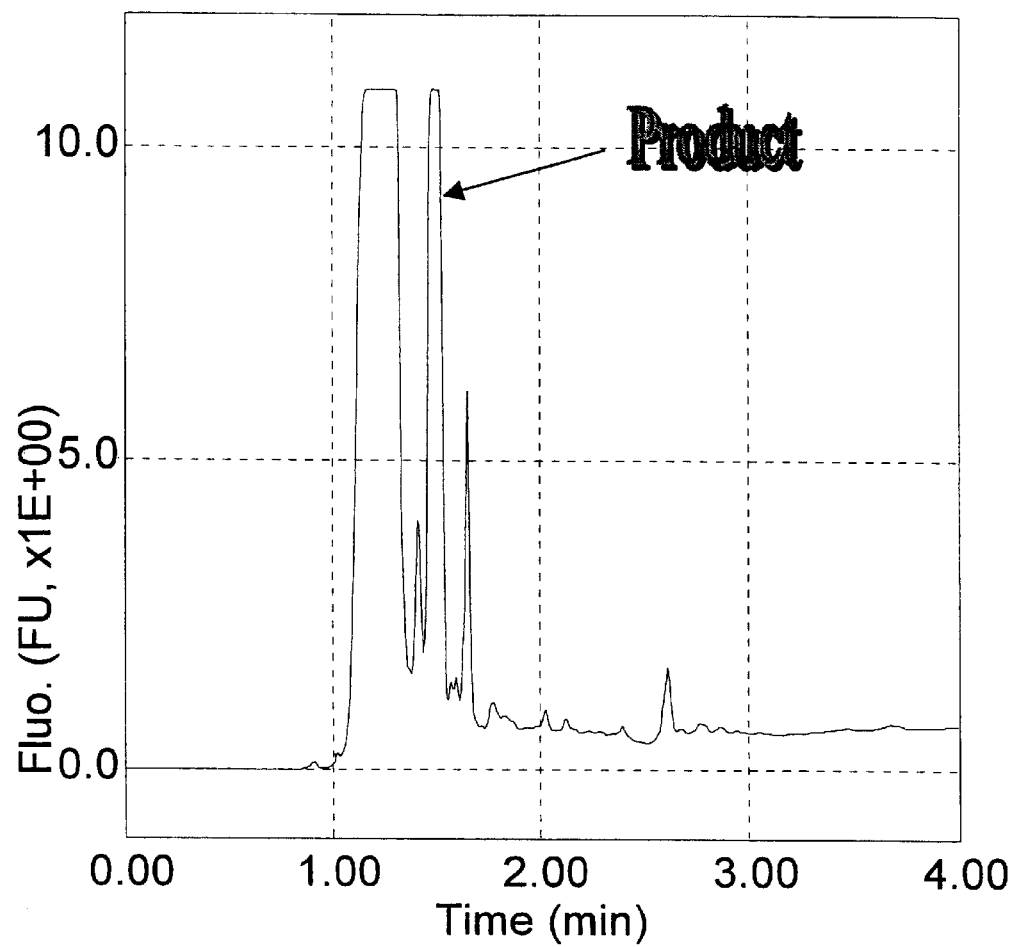
FIG. 13 is an electropherogram of the product of benzaldehyde and fluorescein hydrazine.
Figure 14:
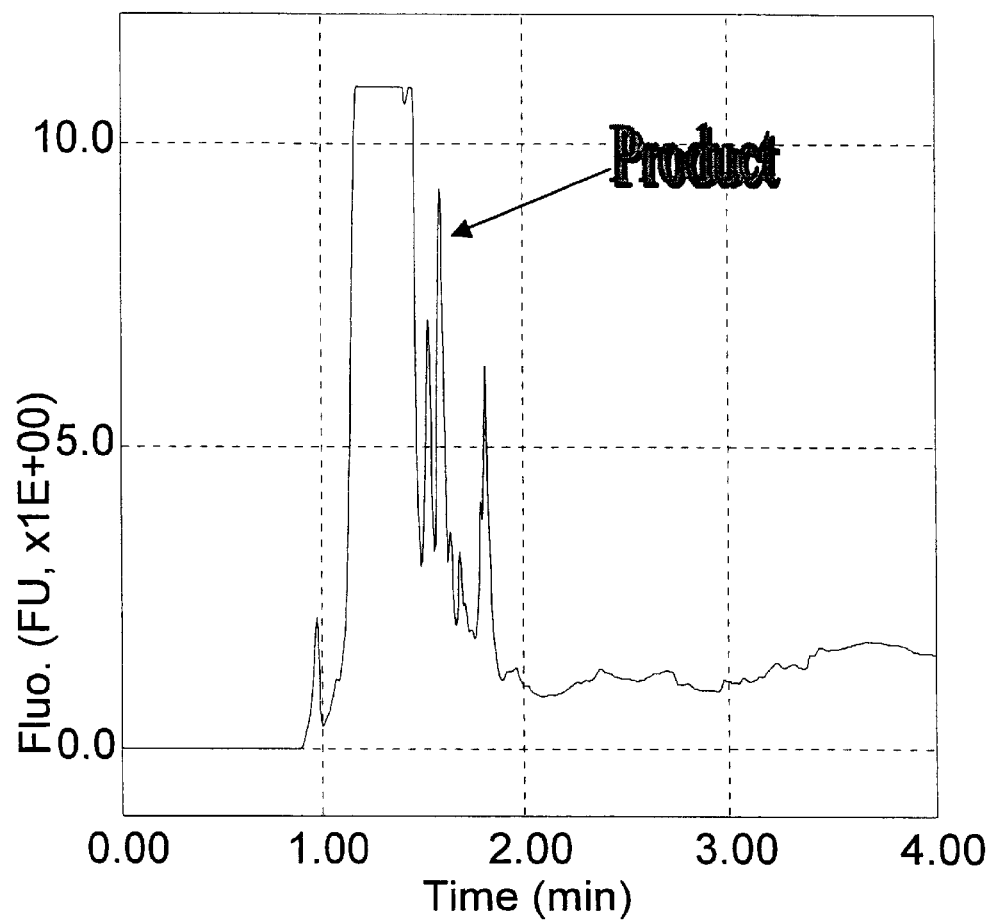
FIG. 14 is an electropherogram of the oxidative product of CYP3A4 and 7-benzyloxyquinoline, followed by reaction with fluorescein hydrazine.
Figure 15:
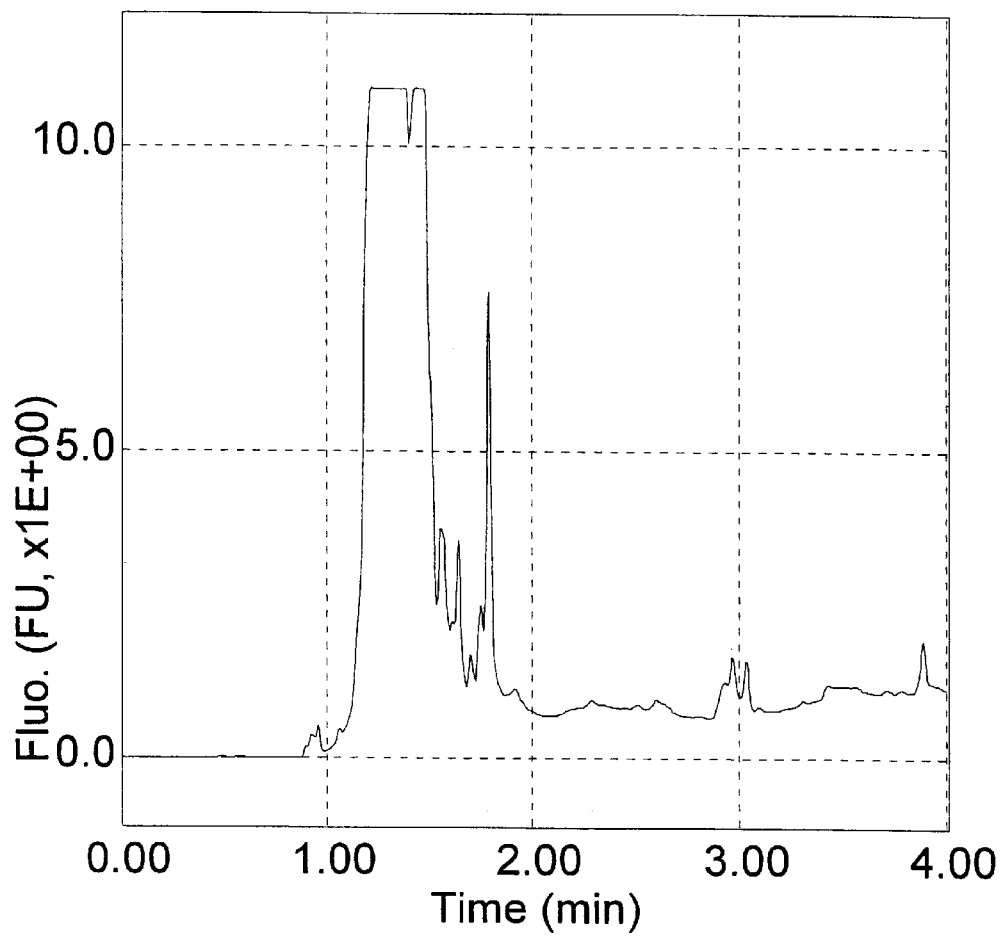
FIGS. 15–17 are electropherograms of control reactions, where enzyme, cofactor or substrate, respectively, are excluded from the reaction.
Figure 16:
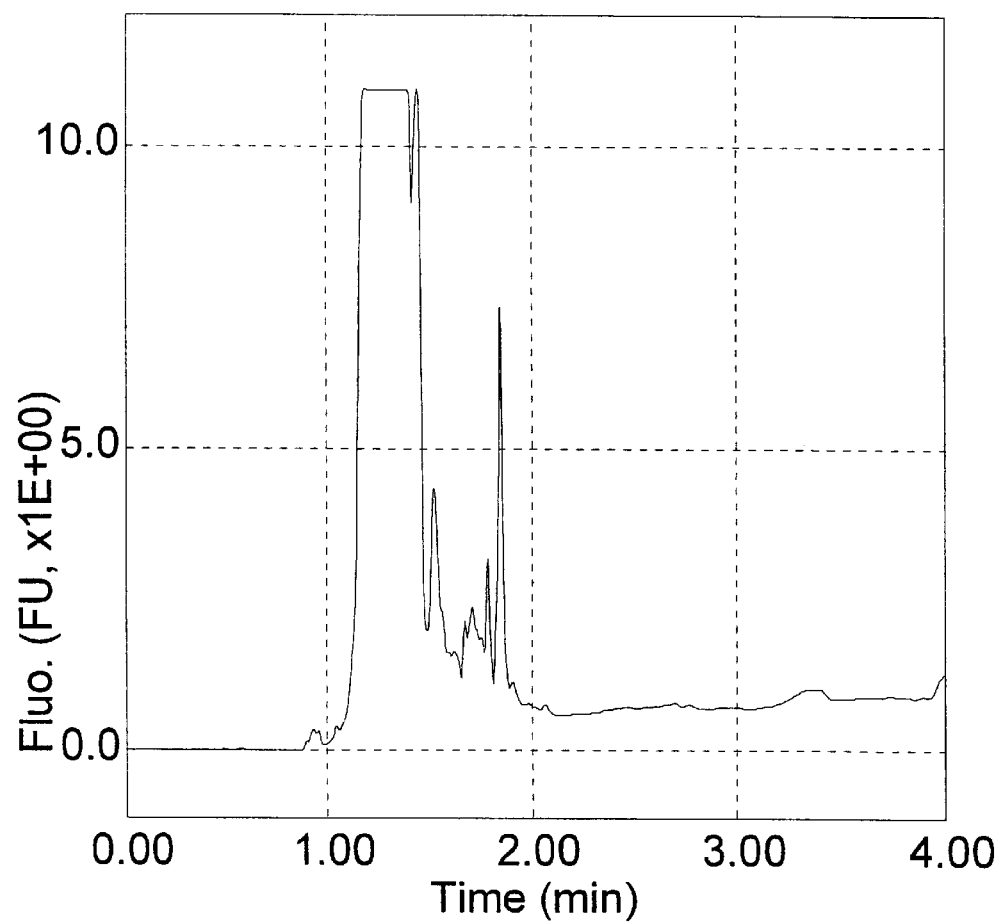
Figure 17:
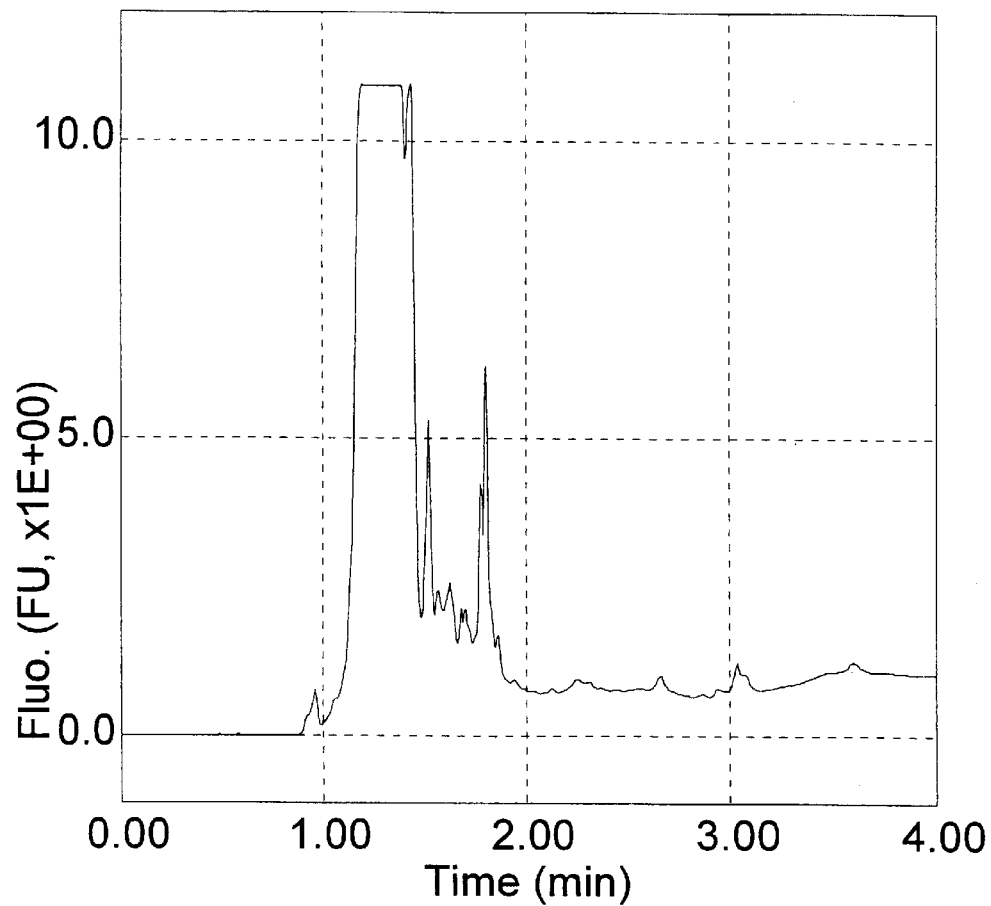

FIG. 13 shows the reaction of benzaldehyde (160 µM) with fluorescein hydrazine under conditions, which are used for the Cytochrome P450 assay. The result from the enzymatic reaction of CYP3A4 with 7-BQ followed by the reaction with fluorescein hydrazine is shown in FIG. 14. As can be seen, the product (benzaldehyde) peak can be clearly identified from the other peaks resulting from either Fl-NH$_2$ or possibly from other enzymatic reaction products. No such a peak was seen in the 1st control (FIG. 15, no enzyme was added), or 2$^{nd}$ control (FIG. 16, no NADPH), or 3$^{rd}$ control (FIG. 17, no 7-BQ).

IV. Comparison of Results from CE and Micro Titer Plate for 7-BQ

Figure 18:
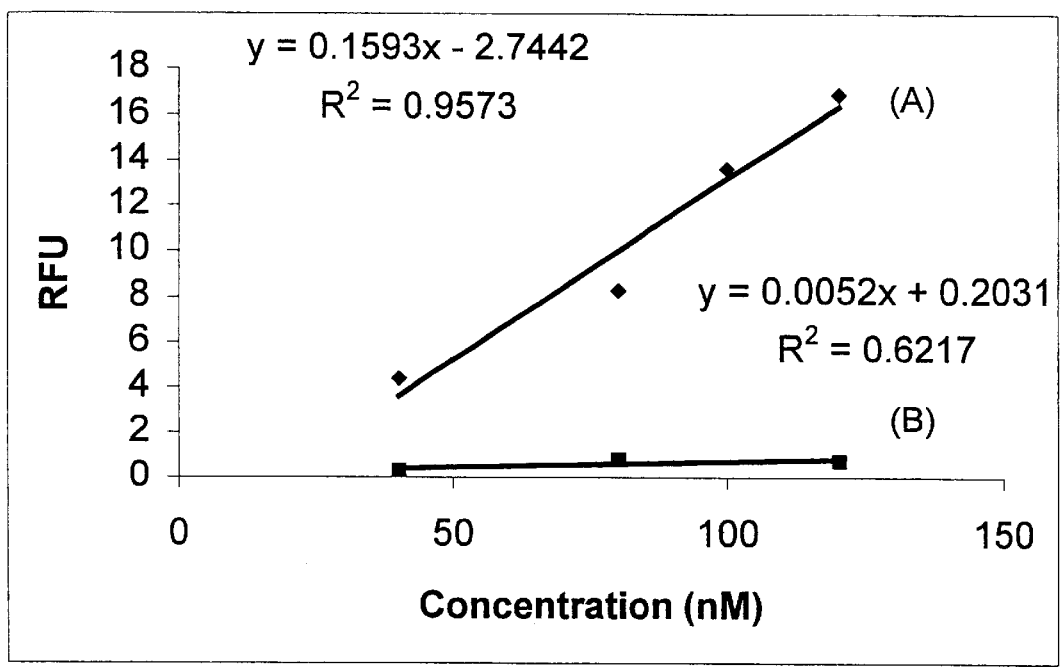
FIG. 18 is a graph of a comparison between capillary electrophoresis (A) and micro titer plate results (B).

FIG. 18 shows the comparison between the sensitivity from the CE and the micro titer plate. As can be seen, a significantly higher sensitivity was achieved with CE as compared to that from the micro titer plate (the slope of calibration curve from CE results was 0.1593 as compared to 0.0052 from the micro titer plate).

V. Preparation of N-(α-hydrazinylacetyl) 5-aminofluorescein

5-Iodoacetamidofluorescein (100 mg, 0.194 mmol) was dissolved in 20 ml of anhydrous ethanol. Hydrazine solution (3.5 ml, 1.0M in THF) was added dropwise at 0° C. while stirring. The color of the reaction mixture changed to dark red shortly after the initial addition of the hydrazine solution. After completion of the addition, the temperature was allowed to increase to room temperature. After two hours, TLC on silica gel (10% MeOH+90% CH$_2$Cl$_2$) showed a new very polar product was formed and some unconverted. Another 3.0 ml of the hydrazine solution was added and the reaction monitored with TLC until starting material was no longer detected. The product precipitated as a red precipitate. The reaction mixture was centrifuged for 5 min, the solvent decanted, and the product dried in vacuo for a few minutes and stored at −80° C. It was used as is. ES/MS for C$_{22}$H$_{17}$N$_3$O$_6$ m/z 420.1 (M+H)$^+$ (100%).

It is evident from the above results that by using cytochrome P-450 substrates having an ether group, which is oxidized to an aldehyde, the subject method provides for a simple rapid and sensitive assay for determining P-450 activity. The rate of reaction at conventional concentrations is rapid and quantitative. The enzyme activity is found to be related to the concentrations of substrate and enzyme and reaches a maximum that is sustained over an extended period of time. Therefore, one may follow the rate of reaction in the early stages of the assay or determine the value, when the rate has leveled off.

All references and patent applications cited herein are incorporated herein by reference, as if they had been set forth in their entirety.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An assay for determining cytochrome P-450 enzyme activity comprising:

combining under conditions for P-450 enzyme activity, a P-450 enzyme, a hydrogen donor cofactor, and at least one substrate characterized by having an ether group bonded to a methylene group, whereby said methylene group is enzymatically oxidized to an aldehyde group;

adding a fluorescent hydrazine to react with said aldehyde group of each of said at least one substrate to form a hydrazone;

quenching enzyme activity with a quencher; and assaying for said hydrazone using capillary electrophoresis, whereby separate peaks are obtained for each at least one substrate.

2. An assay according to claim 1, wherein said methylene group is bonded to an aromatic group.

3. An assay according to claim 1, wherein said methylene group is bonded to an aliphatic group or hydrogen.

4. An assay according to claim 3, wherein said at least one substrate comprises at least one of 7-benzyloxyquinoline and 7-benzyloxyresorufin.

5. An assay according to claim 1, wherein said ether group is a phenolic oxygen and is bonded to a carbocyclic or heterocyclic group.

6. An assay according to claim 1, wherein said combining further comprises an enzyme activating amount of non-ionic detergent.

7. An assay according to claim 1, comprising adding at least two substrates.

8. An assay according to claim 7, wherein said fluorescent hydrazine is fluorescein hydrazine.

9. An assay according to claim 7, wherein the concentration of said enzyme is in the range of about 1 nM to 500 nM.

10. An assay according to claim 7, wherein a reaction volume is in the range of about 0.1 to 50 µl.

11. An assay according to claim 7, wherein said combining further comprises an enzyme activating amount of non-ionic detergent.

12. An assay according to claim 7, comprising adding at least two substrates.

13. An assay for determining cytochrome P-450 enzyme activity comprising:

combining under conditions for P-450 enzyme activity comprising a pH in the range of about 6–8 and a temperature in the range of about 20 to 50° C., a P-450 enzyme, NADPH, and at least one substrate characterized by having an ether group bonded to a methylene group, whereby said methylene group is enzymatically oxidized to an aldehyde group;

adding a fluorescent hydrazine to react with said aldehyde group of each of said at least one substrates to form a hydrazone;

quenching enzyme activity with a quencher; and assaying for said hydrazone using capillary electrophoresis, whereby separate peaks are obtained for each substrate.

* * * * *